US008283326B2

(12) United States Patent
Eckhardt et al.

(10) Patent No.: US 8,283,326 B2
(45) Date of Patent: Oct. 9, 2012

(54) CRYSTALLINE FORM OF 4-(BETA-D-GLUCOPYRANOS-1-YL)-1-METHYL-2-[4-((S)-TETRAHYDROFURAN-3-YLOXY)-BENZYL]-BENZENE, A METHOD FOR ITS PREPARATION AND THE USE THEREOF FOR PREPARING MEDICAMENTS

(75) Inventors: Matthias Eckhardt, Biberach (DE); Frank Himmelsbach, Mittelbiberach (DE); Tanja M. Butz, Merklingen (DE); Hans-Juergen Martin, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 114 days.

(21) Appl. No.: 12/446,003

(22) PCT Filed: Oct. 26, 2007

(86) PCT No.: PCT/EP2007/061553
§ 371 (c)(1),
(2), (4) Date: Jul. 9, 2009

(87) PCT Pub. No.: WO2008/049923
PCT Pub. Date: May 2, 2008

(65) Prior Publication Data
US 2010/0317847 A1 Dec. 16, 2010

(30) Foreign Application Priority Data
Oct. 27, 2006 (EP) ...................... 06123068

(51) Int. Cl.
*A01N 43/04* (2006.01)
*A61K 31/70* (2006.01)
*C07H 1/00* (2006.01)

(52) U.S. Cl. .................... 514/23; 536/1.11; 536/18.7
(58) Field of Classification Search ........................ None
See application file for complete search history.

(56) References Cited

U.S. PATENT DOCUMENTS

| | | | |
|---|---|---|---|
| 7,202,350 B2 | 4/2007 | Imamura et al. | |
| 7,288,528 B2 | 10/2007 | Frick et al. | |
| 7,371,732 B2 | 5/2008 | Eickelmann et al. | |
| 7,375,090 B2 | 5/2008 | Himmelsbach et al. | |
| 7,393,836 B2 | 7/2008 | Eckhardt et al. | |
| 7,417,032 B2 | 8/2008 | Eckhardt et al. | |
| 7,419,959 B2 | 9/2008 | Eckhardt et al. | |
| 7,579,449 B2 | 8/2009 | Eckhardt et al. | |
| 7,662,790 B2 | 2/2010 | Himmelsbach et al. | |
| 7,683,160 B2 | 3/2010 | Eckhardt et al. | |
| 7,687,469 B2 | 3/2010 | Eckhardt et al. | |
| 7,713,938 B2 | 5/2010 | Himmelsbach et al. | |
| 7,723,309 B2 * | 5/2010 | Himmelsbach et al. ........ 514/23 |
| 7,745,414 B2 | 6/2010 | Eckhardt et al. | |
| 7,772,191 B2 | 8/2010 | Eckhardt et al. | |
| 7,772,378 B2 | 8/2010 | Himmelsbach et al. | |
| 7,776,830 B2 | 8/2010 | Eckhardt et al. | |
| 7,847,074 B2 | 12/2010 | Eckhardt et al. | |
| 7,851,602 B2 | 12/2010 | Himmelsbach et al. | |
| 7,858,587 B2 | 12/2010 | Eckhardt et al. | |
| 7,879,806 B2 | 2/2011 | Himmelsbach et al. | |
| 7,879,807 B2 | 2/2011 | Himmelsbach et al. | |
| 8,039,441 B2 | 10/2011 | Himmelsbach et al. | |
| 2003/0114390 A1 | 6/2003 | Washburn et al. | |
| 2004/0138439 A1 | 7/2004 | Deshpande et al. | |
| 2004/0259819 A1 | 12/2004 | Frick et al. | |
| 2005/0187168 A1 | 8/2005 | Eickelmann et al. | |
| 2005/0209166 A1 | 9/2005 | Eckhardt et al. | |
| 2005/0233982 A1 | 10/2005 | Himmelsbach et al. | |
| 2006/0009400 A1 | 1/2006 | Eckhardt et al. | |
| 2006/0019948 A1 | 1/2006 | Eckhardt et al. | |
| 2006/0025349 A1 | 2/2006 | Eckhardt et al. | |
| 2006/0035841 A1 | 2/2006 | Eckhardt et al. | |
| 2006/0063722 A1 | 3/2006 | Washburn et al. | |
| 2006/0074031 A1 | 4/2006 | Eckhardt et al. | |
| 2006/0142210 A1 | 6/2006 | Eckhardt et al. | |
| 2006/0189548 A1 | 8/2006 | Himmelsbach et al. | |
| 2006/0234953 A1 | 10/2006 | Himmelsbach et al. | |
| 2006/0251728 A1 | 11/2006 | Himmelsbach et al. | |
| 2006/0258749 A1 | 11/2006 | Eckhardt et al. | |
| 2007/0004648 A1 | 1/2007 | Himmelsbach et al. | |
| 2007/0027092 A1 | 2/2007 | Himmelsbach et al. | |
| 2007/0049537 A1 | 3/2007 | Eckhardt et al. | |
| 2007/0054867 A1 | 3/2007 | Eckhardt et al. | |
| 2007/0073046 A1 | 3/2007 | Eckhardt et al. | |
| 2007/0249544 A1 | 10/2007 | Himmelsbach et al. | |
| 2007/0259821 A1 | 11/2007 | Eckhardt et al. | |
| 2007/0281940 A1 | 12/2007 | Dugi et al. | |
| 2007/0293690 A1 | 12/2007 | Tomiyama et al. | |
| 2008/0058379 A1 | 3/2008 | Eckhardt et al. | |
| 2009/0023913 A1 | 1/2009 | Eckhardt et al. | |
| 2009/0318547 A1 | 12/2009 | Eckhardt et al. | |
| 2009/0326215 A1 | 12/2009 | Eckhardt et al. | |
| 2010/0069310 A1 | 3/2010 | Himmelsbach et al. | |
| 2010/0081625 A1 | 4/2010 | Wienrich et al. | |
| 2010/0093654 A1 | 4/2010 | Himmelsbach et al. | |
| 2010/0099641 A1 | 4/2010 | Himmelsbach et al. | |
| 2010/0179191 A1 | 7/2010 | Himmelsbach et al. | |
| 2010/0209506 A1 | 8/2010 | Eisenreich | |

(Continued)

FOREIGN PATENT DOCUMENTS

CA 2494177 A1 2/2004
(Continued)

OTHER PUBLICATIONS

Adachi et al., Metabolism, vol. 49(8), Aug. 2000, pp. 990-995.*
International Search Report for PCT/EP2007/061553 mailed Feb. 14, 2008.
U.S. Appl. No. 13/419,784, filed Mar. 14, 2012, Peter Eickelmann, et al., "Inducible Expression of SGLT5, Methods and Kits Using the Same".

*Primary Examiner* — Traviss C McIntosh, III
(74) *Attorney, Agent, or Firm* — Michael P. Morris; Edouard G. Lebel

(57) ABSTRACT

The invention relates to a crystalline form of 4-(β-D-glucopyranos-1-yl)-1-methyl-2-[4-((S)-tetrahydrofuran-3-yloxy)-benzyl]-benzene, to a method for the preparation thereof, as well as to the use thereof for preparing medicaments.

18 Claims, 1 Drawing Sheet

U.S. PATENT DOCUMENTS

| | | |
|---|---|---|
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0098240 A1 | 4/2011 | Dugi et al. |
| 2011/0178033 A1 | 7/2011 | Eckhardt et al. |
| 2011/0195917 A1 | 8/2011 | Dugi et al. |
| 2011/0236477 A1 | 9/2011 | Schneider et al. |
| 2011/0237526 A1 | 9/2011 | Weber et al. |
| 2011/0237789 A1 | 9/2011 | Weber et al. |

FOREIGN PATENT DOCUMENTS

| | | |
|---|---|---|
| CA | 2 557 801 A1 | 10/2005 |
| CA | 2569915 A1 | 1/2006 |
| CA | 2572819 A1 | 1/2006 |
| CA | 2574451 A1 | 2/2006 |
| CA | 2574500 A1 | 4/2006 |
| WO | 9831697 A1 | 7/1998 |
| WO | 0127128 A1 | 4/2001 |
| WO | 02083066 A2 | 10/2002 |
| WO | 03099836 A1 | 12/2003 |
| WO | 2004013118 A1 | 2/2004 |
| WO | 2004052902 A1 | 6/2004 |
| WO | 2004052903 A1 | 6/2004 |
| WO | 2004080990 A1 | 9/2004 |
| WO | 2005012318 A2 | 2/2005 |
| WO | 2005012326 A1 | 2/2005 |
| WO | 2005/092877 A1 | 10/2005 |
| WO | WO2005/092877 * | 10/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006018150 A1 | 2/2006 |
| WO | 2006037537 A2 | 4/2006 |
| WO | 2006064033 A2 | 6/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007031548 A2 | 3/2007 |
| WO | 2007093610 A1 | 8/2007 |
| WO | 2008020011 A1 | 2/2008 |
| WO | 2008034859 A1 | 3/2008 |

* cited by examiner

Figure 1: X-ray powder diffraction pattern of the crystalline form I
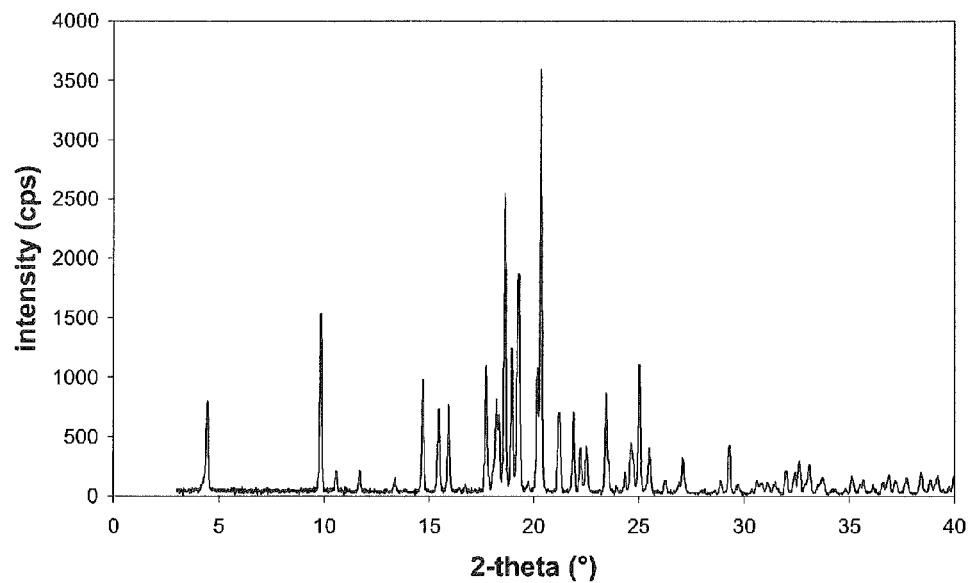
Figure 2: DSC diagram of the crystalline form I
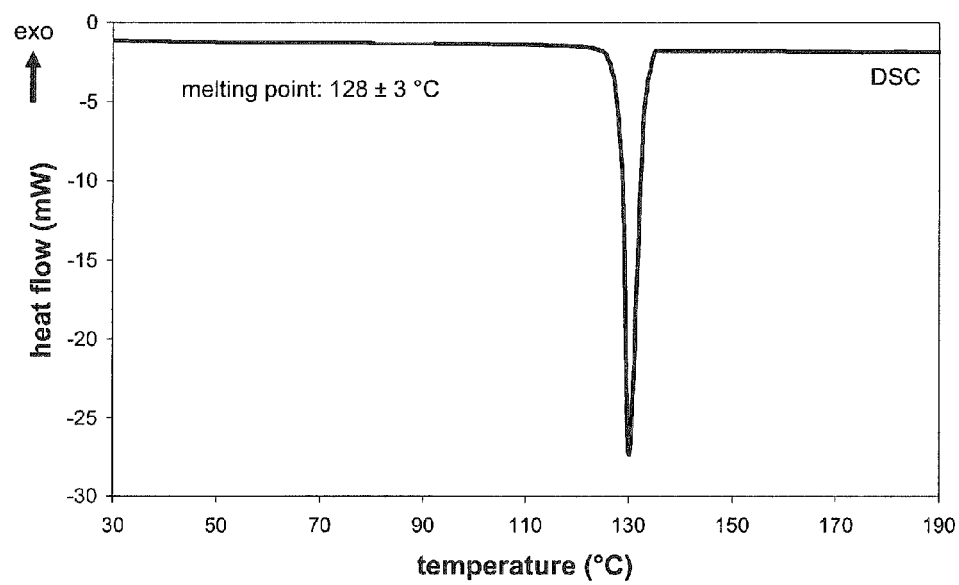

CRYSTALLINE FORM OF 4-(BETA-D-GLUCOPYRANOS-1-YL)-1-METHYL-2-[4-((S)-TETRAHYDROFURAN-3-YLOXY)-BENZYL]-BENZENE, A METHOD FOR ITS PREPARATION AND THE USE THEREOF FOR PREPARING MEDICAMENTS

This application is the national phase entry under 35 U.S.C. §371 of International Application No. PCT/EP2007/061553, filed Oct. 26, 2007, which claims priority to European Application No. EP 06123068.6, filed Oct. 27, 2006, each of which is hereby incorporated by reference in its entirety.

The invention relates to a crystalline form of 4-(β-D-glucopyranos-1-yl)-1-methyl-2-[4-((S)-tetrahydrofuran-3-yloxy)-benzyl]-benzene, to a method for the preparation thereof, as well as to the use thereof for preparing medicaments.

BACKGROUND OF THE INVENTION

The compound 4-(β-D-glucopyranos-1-yl)-1-methyl-2-[4-((S)-tetrahydrofuran-3-yloxy)-benzyl]-benzene (in the following referred to it as "compound A") is described in the international patent application WO 2005/092877 and has the chemical structure according to formula A

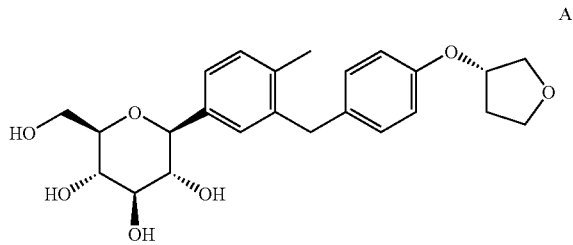

The compounds described therein have a valuable inhibitory effect on the sodium-dependent glucose cotransporter SGLT, particularly SGLT2. The method of manufacture of the compound A as described therein does not yield a crystalline form.

A certain pharmaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronising) has to be avoided as far as possible, in spite of the hard conditions required during the process, it is essential that the active substance should be highly stable throughout the grinding process. Only if the active substance is sufficiently stable during the grinding process it is possible to produce a homogeneous pharmaceutical formulation which always contains the specified amount of active substance in a reproducible manner.

Another problem which may arise in the grinding process for preparing the desired pharmaceutical formulation is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the above-mentioned pharmaceutical compositions under various storage conditions is therefore an additional advantage for both the patient and the manufacturer.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. Preferably, therefore, a pharmaceutically active substance should be only slightly hygroscopic.

Furthermore, the availability of a well-defined crystalline form allows the purification of the drug substance by recrystallization.

Apart from the requirements indicated above, it should be generally borne in mind that any change to the solid state of a pharmaceutical composition which is capable of improving its physical and chemical stability gives a significant advantage over less stable forms of the same medicament.

The aim of the invention is thus to provide a new, stable crystalline form of the compound A which meets important requirements imposed on pharmaceutically active substances as mentioned above.

OBJECT OF THE INVENTION

In a first aspect the present invention relates to a crystalline form of the compound A.

In a second aspect the present invention relates to the crystalline form I of the compound A having an X-ray powder diffraction pattern that comprises peaks at 18.62, 19.27 and 20.35 degrees 2Θ (±0.05 degrees 2Θ, wherein said X-ray powder diffraction pattern is made using CuKα1 radiation).

In another aspect the present invention relates to the compound A wherein at least 50% of said substance is present in the form of the crystalline form as defined hereinbefore and hereinafter.

In the light of the pharmaceutical efficacy of the compound A a third aspect of the present invention relates to a pharmaceutical composition or medicament comprising a crystalline form as defined hereinbefore and hereinafter.

In a further aspect the present invention relates to a use of a crystalline form as defined hereinbefore or hereinafter for preparing a pharmaceutical composition which is suitable for the treatment or prevention of diseases or conditions which can be influenced by inhibiting sodium-dependent glucose cotransporter SGLT, preferably SGLT2.

In a further aspect the present invention relates to a use of a crystalline form as defined hereinbefore or hereinafter for preparing a pharmaceutical composition which is suitable for the treatment or prevention of metabolic disorders.

In a further aspect the present invention relates to a use of a crystalline form as defined hereinbefore or hereinafter for preparing a pharmaceutical composition for inhibiting the sodium-dependent glucose cotransporter SGLT2.

In a further aspect the present invention relates to a use of a crystalline form as defined hereinbefore or hereinafter for preparing a pharmaceutical composition for preventing the degeneration of pancreatic beta cells and/or for improving and/or restoring the functionality of pancreatic beta cells.

In another aspect the present invention relates to a use of a crystalline form as defined hereinbefore and hereinafter for preparing a pharmaceutical composition for preventing, slowing, delaying or treating diseases or conditions attributed to an abnormal accumulation of liver fat in a patient in need thereof.

In a further aspect the present invention relates to a method for making the crystalline form I as defined hereinbefore and hereinafter, said method comprising the following steps:
(a) dissolving compound A in a solvent or a mixture of solvents to form a solution, preferably a saturated, nearly saturated or supersaturated solution;
(b) storing preferably with cooling the solution to precipitate the crystalline form out of solution and thus to yield a suspension;
(c) isolating the precipitate from the suspension; and
(d) drying the precipitate to remove an excess of said solvent or mixture of solvents.

Further aspects of the present invention become apparent to the one skilled in the art from the following detailed description of the invention and the examples.

BRIEF DESCRIPTION OF THE FIGURES

The FIG. 1 shows an X-ray powder diffractogram of the crystalline form I.

The FIG. 2 shows the thermoanalysis and determination of the melting point via DSC of the crystalline form I.

DETAILED DESCRIPTION OF THE INVENTION

Surprisingly, it has been found that there exists a crystalline form of the compound A which fulfills important requirements mentioned hereinbefore. Accordingly the present invention relates to a crystalline form of the compound A.

This crystalline form may be identified by means of their characteristic X-ray powder diffraction (XRPD) patterns.

The crystalline form I is characterised by an X-ray powder diffraction pattern that comprises peaks at 18.62, 19.27 and 20.35 degrees 2Θ (±0.05 degrees 2Θ, wherein said X-ray powder diffraction pattern is made using CuKα1 radiation).

In particular said X-ray powder diffraction pattern comprises peaks at 9.83, 18.62, 18.96, 19.27, 20.18 and 20.35 degrees 2Θ (±0.05 degrees 2Θ, wherein said X-ray powder diffraction pattern is made using CuKα1 radiation).

More specifically, the crystalline form I is characterised by an X-ray powder diffraction pattern, made using CuKα1 radiation, which comprises peaks at degrees 2Θ (±0.05 degrees 2Θ) as contained in Table 1.

TABLE 1

X-ray powder diffraction pattern of the crystalline form I (only peaks up to 30° in 2 Θ are listed):

| 2 Θ [°] | d-value [Å] | Intensity I/I$_0$ [%] |
|---|---|---|
| 4.46 | 19.81 | 22 |
| 9.83 | 8.99 | 42 |
| 10.56 | 8.37 | 5 |
| 11.68 | 7.57 | 5 |
| 13.37 | 6.62 | 3 |
| 14.70 | 6.02 | 26 |
| 15.46 | 5.73 | 20 |
| 15.94 | 5.56 | 21 |
| 16.72 | 5.30 | 2 |
| 17.73 | 5.00 | 29 |
| 18.22 | 4.86 | 22 |
| 18.33 | 4.84 | 17 |
| 18.62 | 4.76 | 72 |
| 18.96 | 4.68 | 33 |
| 19.27 | 4.60 | 52 |
| 19.74 | 4.49 | 2 |
| 20.18 | 4.40 | 30 |
| 20.35 | 4.36 | 100 |
| 21.22 | 4.18 | 20 |
| 21.91 | 4.05 | 19 |
| 22.24 | 3.99 | 10 |
| 22.53 | 3.94 | 11 |
| 23.46 | 3.79 | 24 |
| 23.58 | 3.77 | 8 |
| 23.96 | 3.71 | 2 |
| 24.37 | 3.65 | 5 |
| 24.65 | 3.61 | 12 |
| 25.05 | 3.55 | 30 |
| 25.51 | 3.49 | 10 |
| 26.25 | 3.39 | 3 |
| 26.91 | 3.31 | 3 |
| 27.09 | 3.29 | 8 |
| 28.89 | 3.09 | 3 |
| 29.29 | 3.05 | 11 |
| 29.73 | 3.00 | 2 |

Even more specifically, the crystalline form I is characterised by an X-ray powder diffraction pattern, made using CuKα1 radiation, which comprises peaks at degrees 2Θ (±0.05 degrees 2Θ) as shown in FIG. 1.

Furthermore the crystalline form I of compound A is characterised by a melting point of about 128° C.±3° C. (determined via DSC; evaluated as onset-temperature; heating rate 10 K/min). The obtained DSC curve is shown in FIG. 2.

The X-ray powder diffraction patterns are recorded, within the scope of the present invention, using a STOE-STADI P-diffractometer in transmission mode fitted with a location-sensitive detector (OED) and a Cu-anode as X-ray source (CuKα1 radiation, λ=1,54060 Å, 40 kV, 40 mA). In the Table 1 above the values "2Θ[°]" denote the angle of diffraction in degrees and the values "d-value [Å]" denote the specified distances in Å between the lattice planes. The intensity shown in the FIG. 1 is given in units of cps (counts per second).

In order to allow for experimental error, the above described 2Θ values should be considered accurate to ±0.05 degrees 2Θ. That is to say, when assessing whether a given sample of crystals of the compound A is the crystalline form I in accordance with the invention, a 2Θ value which is experimentally observed for the sample should be considered identical with a characteristic value described above if it falls within ±0.05 degrees 2Θ of the characteristic value.

The melting point is determined by DSC (Differential Scanning Calorimetry) using a DSC 821 (Mettler Toledo).

A further aspect of the present invention relates to a method for making the crystalline form I of the compound A as defined hereinbefore and hereinafter, said method comprising the following steps:
(a) dissolving compound A in a solvent or a mixture of solvents to form a solution, preferably a saturated, nearly saturated or supersaturated solution;
(b) storing the solution to precipitate the crystalline form I out of solution and thus to yield a suspension;
(c) removing the precipitate from the suspension; and
(d) drying the precipitate to remove an excess of said solvent or mixture of solvents.

The terms "saturated" or "nearly saturated" are related to the starting material of the compound A as used in step (a). For example a solution which is saturated or nearly saturated with respect to the starting material of the compound A may be supersaturated with respect to its crystalline form.

Suitable solvents are preferably selected from the group consisting of $C_{1-4}$-alkanols, water, ethylacetate, acetonitrile, acetone, diethylether and mixtures of two or more of these solvents.

More preferred solvents are selected from the group consisting of ethanol, isopropanol, ethyl acetate, diethylether, acetone, water and mixtures of two or more of these solvents.

Particularly preferred solvents are selected from the group consisting of ethylacetate, isopropanol, acetone and water/ethanol mixture.

Preferably the step (a) is carried at about room temperature (about 20° C.) or at an elevated temperature up to about the boiling point of the solvent or mixture of solvents used.

In step (b) the solution is stored for a time sufficient to obtain a precipitate. The temperature of the solution in step (b) is about the same as or lower than in step (a). During the storing the temperature of the solution containing the compound A is preferably lowered, preferably to a temperature in the range of 20° C. to 0° C. or even lower. The step (b) can be carried out with or without stirring. As known to the one skilled in the art by the period of time and the difference of temperature in step (b) the size, shape and quality of the obtained crystals can be controlled. Furthermore the crystallization may be induced by methods as known in the art, for example by mechanical means such as scratching or rubbing the contact surface of the reaction vessel with e.g. a glass rod. Optionally the saturated or supersaturated solution may be inoculated with seed crystals.

In step (c) the solvent(s) can be removed from the precipitate by known methods as for example filtration, suction filtration, decantation or centrifugation.

In step (d) an excess of the solvent(s) is removed from the precipitate by methods known to the one skilled in the art as for example by reducing the partial pressure of the solvent(s), preferably in vacuum, and/or by heating above ca. 20° C., preferably in a temperature range below 80° C., even more preferably below 50° C.

The compound A may be synthesized by methods as specifically and/or generally described or cited in the international application WO 2005/092877. Furthermore the biological properties of the compound A may be investigated as it is described in the international application WO 2005/092877 which in its enterity is incorporated herein by reference.

The crystalline form in accordance with the invention is preferably employed as drug active substance in substantially pure form, that is to say, essentially free of other crystalline forms of the compound A. Nevertheless, the invention also embraces the crystalline form in admixture with another crystalline form or forms. Should the drug active substance be a mixture of crystalline forms, it is preferred that the substance comprises at least 50% of the crystalline form I as described herein.

In view of their ability to inhibit the SGLT activity, the crystalline form according to the invention is suitable for the preparation of pharmaceutical compositions for the treatment and/or preventative treatment of conditions or diseases which may be affected by the inhibition of the SGLT activity, particularly the SGLT-2 activity. Therefore, the crystalline form I is particularly suitable for the preparation of pharmaceutical compositions for prevention or treatment of diseases, particularly metabolic disorders, or conditions such as type 1 diabetes mellitus, type 2 diabetes mellitus, complications of diabetes (such as e.g. retinopathy, nephropathy or neuropathies, diabetic foot, ulcers, microangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. The crystalline form is also suitable for the preparation of pharmaceutical compositions for preventing beta-cell degeneration such as e.g. apoptosis or necrosis of pancreatic beta cells. The crystalline form is also suitable for the preparation of pharmaceutical compositions for improving or restoring the functionality of pancreatic cells, and also of increasing the number and size of pancreatic beta cells. The crystalline form according to the invention may also be used for the preparation of pharmaceutical compositions useful as diuretics or antihypertensives and suitable for the prevention and treatment of acute renal failure.

By the administration of the crystalline form according to this invention an abnormal accumulation of fat in the liver may be reduced or inhibited. Therefore according to another aspect of the present invention there is provided a method for preventing, slowing, delaying or treating diseases or conditions attributed to an abnormal accumulation of liver fat in a patient in need thereof characterized in that a pharmaceutical composition according to the present invention is administered. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimentation-induced fatty liver, diabetic fatty liver, alcoholic-induced fatty liver or toxic fatty liver.

In particular, the crystalline form according to the invention is suitable for the preparation of pharmaceutical compositions for the prevention or treatment of diabetes, particularly type 1 diabetes mellitus, type 2 diabetes mellitus, and/or diabetic complications.

In addition the crystalline form according to the invention is particularly suitable for the prevention or treatment of overweight, obesity (including class I, class II and/or class III obesity), visceral obesity and/or abdominal obesity.

The dosage required to achieve the corresponding activity for treatment or prevention usually depends on the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, the pharmaceutical compositions according to this invention preferably comprise the crystalline form together with one or more inert conventional carriers and/or diluents. Such pharmaceutical compositions may be formulated as conventional galenic preparations such as plain or coated tablets, capsules, powders, suspensions or suppositories.

The following example of synthesis serves to illustrate a method of preparing the compound A and its crystalline form I. It is to be regarded only as a possible method described by way of example, without restricting the invention to its contents. In the following the term "ambient temperature" denotes a temperature of about 20° C.

Preparation of the Starting Compounds:

Example I

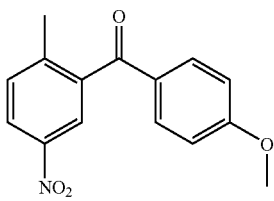

(2-Methyl-5-nitro-phenyl)-(4-methoxy-phenyl)-methanone

To a mixture of 2-methyl-5-nitro-benzoic acid (50 g) in dichloromethane (330 mL) is added oxalyl chloride (25.5 mL) followed by dimethylformamide (0.5 mL). The reaction mixture is stirred at ambient temperature for 14 h, then filtered and separated from all volatile constituents in a rotary evaporator. The residue is dissolved in dichloromethane (100 mL), the resulting solution is cooled to −5° C., and anisole (31 mL) is added. Then aluminum trichloride (37.5 g) is added batchwise so that the temperature maintains below 5° C. The solution is stirred for another 1 h at 1 to 5° C. and then poured onto crushed ice. The organic phase is separated and the aqueous phase is extracted with dichloromethane. The combined organic phases are washed with aqueous hydrochloric acid (1 mol/L), twice with aqueous sodium hydroxide solution (1 mol/L) and with brine. The organic phase is dried (sodium sulphate), the solvent is removed and the residue is recrystallised from ethanol.

Yield: 65.8 g (88% of theory); Mass spectrum (ESI$^+$): m/z=272 [M+H]$^+$

Example II

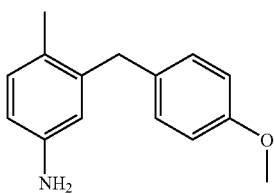

4-Amino-2-(4-methoxy-benzyl)-1-methyl-benzene

A mixture of (2-methyl-5-nitro-phenyl)-(4-methoxy-phenyl)-methanone (5.8 g) and 10% Pd on carbon (1.0 g) in ethyl acetate (200 mL) is shaken under hydrogen atmosphere (7 bar) at ambient temperature for 4.5 h. The solution is separated from the palladium catalyst by filtration and the filtrate is concentrated in vacuo to give a mixture of the title compound, (5-amino-2-methyl-phenyl)-(4-methoxy-phenyl)-methanone and (5-amino-2-methyl-phenyl)-(4-methoxy-phenyl)-methanol. This compound mixture is dissolved in a mixture of acetonitrile (12 mL) and dichloromethane (8 mL) and the resulting solution is cooled in an ice-bath. Triethylsilane (20 mL) is added followed by the slow addition of boron trifluoride diethyl etherate (16 mL). The solution is stirred for 0.5 h at 5° C. and then quenched by the addition of aqueous sodium hydroxide solution (2 mol/L). The organic phase is separated and the aqueous phase is extracted with dichloromethane. The combined organic phases are washed with brine, dried (sodium sulphate) and concentrated in vacuo. The residue is purified by chromatography on silica gel (cyclohexane/ethyl acetate 9:1->2:1).

Yield: 4.0 g (82% of theory)
Mass spectrum (ESI$^+$): m/z=228 [M+H]$^+$

Example III

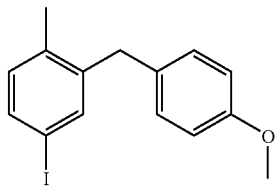

4-Iodo-2-(4-methoxy-benzyl)-1-methyl-benzene

To a cooled (0 to −5° C.), stirred suspension of 4-amino-2-(4-methoxy-benzyl)-1-methyl-benzene (18.3 g) in water (70 mL) and concentrated hydrochloric acid (20 mL) is added a solution of sodium nitrite (5.8 g) in water (20 mL). The suspension is stirred until homogenous and then a solution of potassium iodide (14 g) in water (20 mL) is added. The cooling bath is removed and the solution is stirred at 40° C. for 1 h and at 70° C. for another 1.5 h. After cooling to ambient temperature, aqueous sodium thiosulfate solution is added and the resulting solution is extracted with ethyl acetate. The combined extracts are dried (sodium sulphate) and the solvent is evaporated. The residue is purified by chromatography on silica gel (cyclohexane/ethyl acetate 19.1).

Yield: 18.1 g (66% of theory)
Mass spectrum (EI): m/z=338 [M]$^+$

Example IV

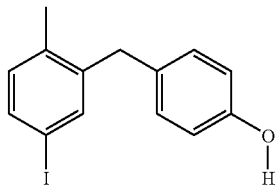

4-(5-Iodo-2-methyl-benzyl)-phenol

To an ice-cold solution of 4-iodo-2-(4-methoxy-benzyl)-1-methyl-benzene (12.5 g) in dichloromethane (70 mL) is added a solution of boron tribromide in dichloromethane (1 mol/L, 40 mL). The resulting solution is stirred in the ice-bath for 1 h and at ambient temperature overnight. The solution is then cooled in an ice bath and saturated aqueous potassium carbonate solution is added dropwise. At ambient temperature the mixture is adjusted with aqueous hydrochloric acid (1 mol/L) to a pH of 1, the organic phase is separated, and the aqueous phase is extracted with dichloromethane. The combined organic phases are dried (sodium sulphate) and concentrated in vacuo to give the crude product.

Yield: 12.0 g (100% of theory)

Example V

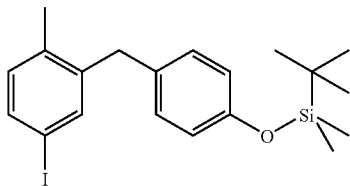

[4-(5-Iodo-2-methyl-benzyl)-phenoxy]-tert-butyl-dimethyl-silane

To an ice cooled solution of 4-(5-iodo-2-methyl-benzyl) phenol (12.0 g) and imidazole (3.2 g) in dimethylformamide (40 mL) is added tert-butyldimethyl-chlorosilane (6.1 g). The ice-bath is removed and the solution is stirred at ambient temperature overnight. The solution is diluted with ethyl acetate and washed twice with hydrochloric acid (1 mol/L). The organic phase is dried (sodium sulphate) and concentrated in vacuo. The residue is purified by chromatography on silica gel (cyclohexane/ethyl acetate 1:0->20:1).

Yield: 9.6 g (59% of theory)
Mass spectrum (ESI): m/z=439 [M+H]$^+$

Example VI

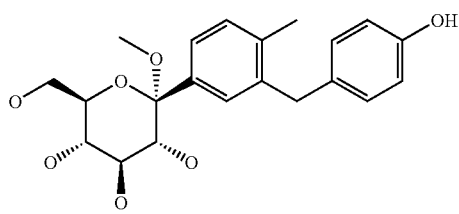

2-(4-Hydroxybenzyl)-4-(1-methoxy-β-D-glucopyranos-1-yl)-1-methyl-benzene

A solution of [4-(5-iodo-2-methyl-benzyl)-phenoxy]-tert-butyl-dimethyl-silane (4.3 g) in dry tetrahydrofuran (50 mL) is cooled to −80° C. under argon atmosphere. Butyllithium (1.6 mol/L in hexane, 7.0 mL) is added dropwise and the resultant solution is stirred for 45 min at −78° C. Then a solution of 2,3,4,6-tetrakis-O-(trimethylsilyl)-D-glucopyranone (6.0 g) in tetrahydrofuran (30 mL) chilled to −80° C. is added via transfer canula. The resulting solution is stirred for 3 h at −78° C. and then quenched with acetic acid in water (1% acetic acid, 100 mL). The organic layer is separated and the aqueous layer is extracted with ethyl acetate. The combined organic phases are washed with brine, dried (sodium sulphate) and concentrated. The residue is taken up in methanol (30 mL) and treated with methanesulfonic acid (20 μL). The resulting solution is stirred at ambient temperature overnight. Triethylamine (2 mL) is added and the solution is concentrated under reduced pressure. Ethyl acetate is added and the resulting mixture is washed with aqueous sodium hydrogencarbonate solution, dried (sodium sulphate) and concentrated to give the crude product.

Yield: 3.4 g (89% of theory)
Mass spectrum (ESI$^-$): m/z=389 [M−H]$^-$

Example VII

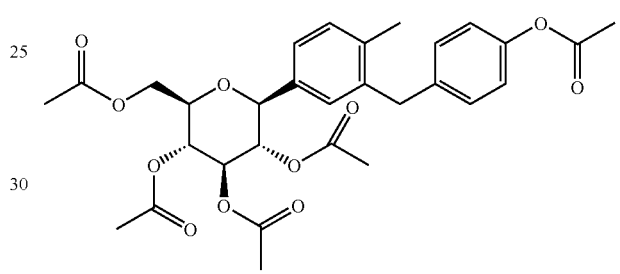

2-(4-Acetoxybenzyl)-1-methyl-4-(2,3,4,6-tetra-O-acetyl-β-D-glucopyranos-1-yl)-benzene A solution of 2-(4-hydroxybenzyl)-4-(1-methoxy-β-D-glucopyranos-1-yl)-1-methyl-benzene (3.4 g) and triethylsilane (2.9 mL) in a mixture of acetonitrile (100 mL) and dichloromethane (40 mL) is cooled to −20° C. Boron trifluoride diethyl etherate (1.7 mL) is added dropwise and the solution is allowed to warm to 0° C. After 30 min of stirring, aqueous potassium hydroxide solution (4 mol/L, 9 mL) is added and the resulting solution is stirred for 15 min at ambient temperature. The solution is adjusted to pH 5 by addition of hydrochloric acid (1 mol/L) and extracted with ethyl acetate. The combined organic phases are washed with brine, dried (sodium sulphate) and concentrated. The residue is dissolved in dichloromethane (50 mL) and pyridine (5 mL), acetic anhydride (5 mL) and 4-dimethylaminopyridine (0.1 g) are consecutively added. After stirring at ambient temperature for 4 h, aqueous sodium bicarbonate solution is added and the resulting mixture is stirred for 10 min. Then the organic phase is separated and the aqueous phase is extracted with ethyl acetate. The combined organic phases are washed with hydrochloric acid (1 mol/L), dried (sodium sulphate) and concentrated. The residue is recrystallized form ethanol to give the pure product.

Yield: 1.8 g (37% of theory)
Mass spectrum (ESI$^+$): m/z=588 [M+NH$_4$]$^+$

Example VIII

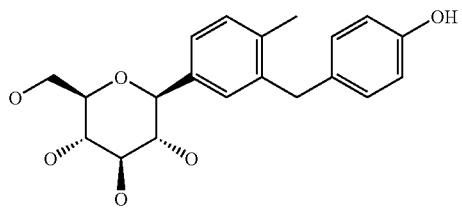

4-(β-D-glucopyranos-1-yl)-2-(4-hydroxy-benzyl)-1-methyl-benzene

A solution of 2-(4-acetoxybenzyl)-1-methyl-4-(2,3,4,6-tetra-O-acetyl-β-D-glucopyranos-1-yl)-benzene (1.8 g) in a mixture of methanol (30 mL) and tetrahydrofuran (15 mL) is treated with aqueous potassium hydroxide solution (4 mol/L, 3.8 mL). The reaction solution is stirred at ambient temperature for 30 min and then neutralized with hydrochloric acid (1 mol/L). The resulting mixture is concentrated under reduced pressure, diluted with aqueous sodium bicarbonate solution and extracted with ethyl acetate. The combined organic phases are dried (sodium sulphate) and concentrated.

Yield: 1.18 g (100% of theory)
Mass spectrum (ESI+): m/z=378 [M+NH$_4$]+
Preparation of the Compound A:

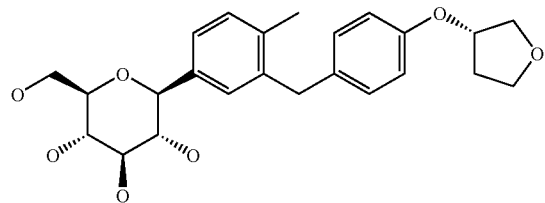

4-(β-D-qlucopyranos-1-yl)-1-methyl-2-[4-((S)-tetrahydrofuran-3-yloxy)-benzyl]-benzene (R)-3-(4-methylphenylsulfonyloxy)-tetrahydrofuran (4.9 g) is added to a mixture of 4-(β-D-glucopyranos-1-yl)-2-(4-hydroxy-benzyl)-1-methyl-benzene (4.9 g) and cesium carbonate (6.6 g) in dimethylformamide (50 mL). The mixture is stirred at 60° C. for 8 h, before more cesium carbonate (0.7 g) and (R)-3-(4-methylphenyl-sulfonyloxy)-tetrahydrofuran (0.5 g) are added. After an additional 14 h stirring at 80° C., the mixture is cooled to ambient temperature, diluted with ethyl acetate and washed with brine. The organic phase is dried (sodium sulphate) and the solvent is removed. The residue is purified by chromatography on silica gel (dichloromethane/methanol 1:0->4:1).

Yield: 2.68 g (46% of theory)
Mass spectrum (ESI+): m/z=448 [M+NH$_4$]+
Preparation of the Crystalline Form I:
4-(β-D-glucopyranos-1-yl)-1-methyl-2-[4-((S)-tetrahydrofuran-3-yloxy)-benzyl]-benzene (2.6 g, obtained as described above) is dissolved in ethyl acetate (10 mL) upon heating up to about 50° C. The solution is allowed to cool slowly (about 1 to 3 h) to about 20° C. After 48 h the crystalline form I is isolated as white crystals by filtration. An excess of the solvent is removed by storing the crystals at elevated temperature (40 to 50° C.) for about 3 to 4 h at reduced pressure.

The invention claimed is:
1. A crystalline form of 4-(β-D-glucopyranos-1-yl)-1-methyl-2-[4-((S)-tetrahydrofuran-3-yloxy)-benzyl]-benzene having an X-ray powder diffraction pattern that comprises peaks at 18.62, 19.27 and 20.35 degrees 2Θ (±0.05 degrees 2Θ), wherein said X-ray powder diffraction pattern is made using CuKα1 radiation.

2. The crystalline form according to claim 1, wherein the X-ray powder diffraction pattern further comprises peaks at 9.83, 18.96 and 20.18 degrees 2Θ (±0.05 degrees 2Θ), wherein said X-ray powder diffraction pattern is made using CuKα1 radiation.

3. 4-(β-D-glucopyranos-1-yl)-1-methyl-2-[4-((S)-tetrahydrofuran-3-yloxy)-benzyl]-benzene wherein at least 50% of said substance is present in the form of the crystalline form in accordance with claim 1.

4. A pharmaceutical composition comprising the crystalline form in accordance with claim 1.

5. Method for the treatment of diseases or conditions which can be influenced by inhibiting the sodium-dependent glucose cotransporter SGLT comprising administering to a patient a crystalline form in accordance to claim 1.

6. Method for the treatment of metabolic disorders, in particular of a metabolic disorder selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia comprising administering to a patient a crystalline form in accordance to claim 1.

7. Method for inhibiting the sodium-dependent glucose cotransporter SGLT2 comprising administering to a patient a crystalline form in accordance to claim 1.

8. Method for treating the degeneration of pancreatic beta cells and/or for improving and/or restoring the functionality of pancreatic beta cells SGLT2 comprising administering to a patient a crystalline form in accordance to claim 1.

9. Method for preventing, slowing, delaying or treating diseases or conditions attributed to an abnormal accumulation of liver fat in a patient in need thereof SGLT2 comprising administering to a patient a crystalline form in accordance to claim 1.

10. A method for making the crystalline form in accordance with claim 2, said method comprising the following steps:
(a) dissolving 4-(β-D-glucopyranos-1-yl)-1-methyl-2-[4-(S)-tetrahydrofuran-3-yloxy)-benzyl]-benzene in a solvent or a mixture of solvents to form a solution;
(b) storing the solution to precipitate the crystalline form in accordance with claim 1 out of solution and thus to yield a suspension;
(c) isolating the precipitate from the suspension; and
(d) drying the precipitate to remove an excess of said solvent or mixture of solvents.

11. 4-(β-D-glucopyranos-1-yl)-1-methyl-2- [4((S)-tetrahydrofuran-3-yloxy)-benzyl]-benzene wherein at least 50% of said substance is present in the form of the crystalline form in accordance with claim 3.

12. A pharmaceutical composition comprising the crystalline form in accordance with claim 3.

13. Method for the treatment of diseases or conditions which can be influenced by inhibiting the sodium-dependent glucose cotransporter SGLT comprising administering to a patient a crystalline form in accordance to claim 3.

14. Method for the treatment of metabolic disorders selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia comprising administering to a patient a crystalline form in accordance to claim 3.

15. Method for inhibiting the sodium-dependent glucose cotransporter SGLT2 comprising administering to a patient a crystalline form in accordance to claim 3.

16. Method for treating the degeneration of pancreatic beta cells and/or for improving and/or restoring the functionality of pancreatic beta cells SGLT2comprising administering to a patient a crystalline form in accordance to claim 3.

17. Method for slowing, delaying or treating diseases or conditions attributed to an abnormal accumulation of liver fat in a patient in need thereof SGLT2comprising administering to a patient a crystalline form in accordance to claim 3.

18. A method for making the crystalline form in accordance with claim 3, said method comprising the following steps: (a) dissolving 4-(β-D-glucopyranos-1-yl)-1-methyl-2-[4-((S)-tetrahydrofuran-3-yloxy)- benzyl]-benzene in a solvent or a mixture of solvents to form a solution; (b) storing the solution to precipitate the crystalline form in accordance with claim 2 out of solution and thus to yield a suspension; (c) isolating the precipitate from the suspension; and (d) drying the precipitate to remove an excess of said solvent or mixture of solvents.

* * * * *